(12) United States Patent
Mukai et al.

(10) Patent No.: US 7,144,585 B1
(45) Date of Patent: Dec. 5, 2006

(54) CILOSTAZOL PREPARATION

(75) Inventors: Tadashi Mukai, Naruto (JP); Yuso Tomohira, Tokushima (JP); Masafumi Toda, Naruto (JP); Keigo Yamada, Tokushima (JP); Yoshikazu Oka, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/555,026

(22) PCT Filed: Mar. 21, 2000

(86) PCT No.: PCT/JP00/01722

§ 371 (c)(1),
(2), (4) Date: Jan. 18, 2002

(87) PCT Pub. No.: WO00/57881

PCT Pub. Date: Oct. 5, 2000

(30) Foreign Application Priority Data

Mar. 25, 1999 (JP) .................................. 11/81363
Sep. 30, 1999 (JP) ................................ 11/279147

(51) Int. Cl.
*A61K 9/14* (2006.01)
*A61K 9/20* (2006.01)
*A61K 9/48* (2006.01)

(52) U.S. Cl. ...................... 424/452; 424/455; 424/463; 424/465; 424/474; 424/489; 424/490; 514/951; 514/952; 514/960; 514/961; 514/962; 514/963; 514/964

(58) Field of Classification Search ................ 514/314, 514/312, 951, 952, 960–965; 424/452, 457, 424/458, 465, 468, 469, 470–472, 474, 489, 424/490

See application file for complete search history.

(56) References Cited

U.S. PATENT DOCUMENTS

| | | | |
|---|---|---|---|
| 4,344,934 | A | 8/1982 | Martin et al. |
| 4,892,741 | A | 1/1990 | Ohm et al. |
| 4,895,726 | A | 1/1990 | Curtet et al. |
| 5,145,684 | A | 9/1992 | Liversidge et al. |
| 5,202,129 | A | 4/1993 | Samejima et al. .......... 424/489 |
| 5,624,683 | A | 4/1997 | Andoh et al. |
| 5,849,330 | A | 12/1998 | Marvola et al. |
| 6,117,455 | A * | 9/2000 | Takada et al. .............. 424/501 |
| 6,264,922 | B1 * | 7/2001 | Wood et al. .................. 424/45 |
| 6,294,192 | B1 * | 9/2001 | Patel et al. .................. 424/451 |
| 6,825,214 | B1 * | 11/2004 | Mendelovici et al. ....... 514/312 |
| 2005/0255155 | A1 * | 11/2005 | Sen et al. ................... 424/451 |

FOREIGN PATENT DOCUMENTS

| | | |
|---|---|---|
| EP | 0 179 583 A1 | 4/1986 |
| EP | 0 661 045 A1 | 5/1995 |
| JP | 7-291869 | 11/1995 |
| JP | 10-67657 | 3/1998 |
| WO | WO 93/05770 | 4/1993 |
| WO | WO 96/21448 | 7/1996 |
| WO | WO 97/48382 | * 12/1997 |
| WO | WO PCT 97/18382 | * 12/1997 |
| WO | WO 98/31360 | 7/1998 |

OTHER PUBLICATIONS

"Pharmacokinetics vol. 13, Supplement (1998), S 169, 11B16-4 Analysis of mechanism on improving mucosa lesion caused by intermediate chain-fatty acid salt according to amino acid," with English translation.

"Bronchoprotective Effect of an Intrabronchial Administration of Cilostazol Powder and a Nebulized PDE1 and PDE4 Inhibitor KF19514 in Guinea Pigs," M. Fujimura et al., International Archives of Allergy and Immunology, vol. 116, No. 3, 1998, pp. 220-227.

"Pharmazeutisch-technologische," H. Sucker et al.. 1991, Thieme Verlag., Stuttgart XP002145328 189560, pp. 673-675.

Carmona-Ibáñez, Gisela et al., "Experimental Studies on the Influence of Surfactants on Intestinal Absorption of Drugs", Arzneim. Forsch./Drug Res. 49(I), Nr. 1 pp. 44-50, (1999).

Sancho-Chust, V. et al., "Experimental Studies on the Influence of Surfactants on Intestinal Absorption of Drugs", Arzneim.Forsch./Drug Res. 45(I), Nr. 5 pp. 595-601, (1995).

Garrigues, T.M. et al., "Absorption-partition Relationships for True Homologous Series of Xenobiotics as a Possible Approach to Study Mechanisms of Surfactants in Absorption. Iv. Phenylacetic Acid Derivatives", International Journal of Pharmaceutics, 79 pp. 135-140, (1992).

* cited by examiner

*Primary Examiner*—Frederick Krass
(74) *Attorney, Agent, or Firm*—Finnegan, Henderson, Farabow, Garrett & Dunner, L.L.P.

(57) ABSTRACT

Provided is a cilostazol preparation which comprises incorporating a fine powder of cilostazol into a dispersing and/or solubilizing agent thereby to enhance the dispersibility and/or solubility. Further, provided is a process for improving absorbability of a slightly soluble drug such as cilostazol even at the lower portion of the digestive tract, wherein said drug is hard to be absorbed at the lower portion of the digestive tract when a conventional method is used. According to the present invention, cilostazol is absorbed enough even at the lower portion of the digestive tract to have an effect as thrombolytic drug, cerebral circulation improving drug or the like.

19 Claims, 5 Drawing Sheets

CILOSTAZOL PREPARATION

This application is a 371 of PCT/JP00/01722, filed Mar. 21, 2000

TECHNICAL FIELD

The present invention relates to a preparation wherein the absorbability of cilostazol, which is commercially available as thrombolytic drug, cerebral circulation improving drug or the like is improved and, more particularly, to a preparation comprising a fine powder of cilostazol as an active ingredient wherein the bioabsorbability, particularly the absorbability at the lower portion of the digestive tract is improved.

BACKGROUND ART

Cilostazol (general name of 6-[4-(1-cyclohexyl-1H-tetrazol-5-yl)butoxy]-3,4-dihydrocarbostyryl) has widely been used as thrombolytic drug, cerebral circulation improving drug, anti-phlogistic drug, anti-ulcer drug, hypotensive drug, drug for asthema, and phosphodiesterase inhibitor because it shows not only a high platelet aggregation supression action but also a phosphodiesterase inhibition action, an anti-ulcer action, a hypotensive action and an anti-phlogistic action. Cilostazol is usually used in the form of a tablet produced by adding excipients and other ingredients and compressing the mixture, and is orally administered. However, since the tablet is quickly disintegrated in the living body when orally administered, a large amount of cilostazol is released in the living body within a short time thereby to cause high concentration in blood, resulting in side effects such as headache, heavy feel in head, or pain. To prevent these side effects, a measure of administering a low-dose tablet in multiple dosing is suggested. However, it is ideal to produce a preparation capable of sustaining mild absorption for a long time by a single administration in order to avoid a complicated administration as much as possible. A fixed concentration of a drug in blood can be maintained by forming a slightly soluble drug into a sustained release preparation. However, since cilostazol is mainly absorbed at the upper portion of the digestive tract when administered orally and the absorption rate at the lower portion of the digestive tract is not sufficient, a single administration has its limits of the duration time of absorption. Accordingly, it becomes possible to maintain the concentration of cilostazol within desirable range in blood for a long time by improving absorption at the lower portion of the digestive tract.

Japanese Laid-open Patent Publication No. 7-291869 discloses that bioavailability of certain pharmaceutical agents is remarkably increased by forming a phosphonic acid diester derivative into a fine powder (average particle diameter of not more than about 10 μm).

However, when cilostazol was simply formed into a fine powder of less than about 10 μm in average particle diameter, its absorption rate at the lower portion of the digestive tract was very low.

U.S. Pat. No. 5,145,684 discloses particles consisting essentially of a crystalline drug substance having a surface modifier absorbed on the surface in amount sufficient to maintain an effective average particle size of less than about 400 nm wherein the bioavailability is increased.

But, this USP does not describe increasing the absorption rate at the lower portion of the digestive tract, of slightly soluble drug which exhibits an extremely low adsorption rate thereat.

WO 96/21448 discloses a resin particle having a particle size of not greater than 2,000 μm, which comprises an ethylene vinyl alcohol copolymer and 5 to 10% by weight of cilostazol incorporated therein. The resin particle, upon being administered orally, allows the concentration of cilostazol in blood to be kept constant over an extended period of time.

However, a production method of the resin particle is attended with many problems that an apparatus is on a large scale and an elevated temperature is required, and so on.

Japanese Laid-open Patent Publication No. 10-67657 discloses a multiple-unit type sustained release preparation, which contains two sustained release small tablets prepared by incorporating hydroxypropylmethylcellulose as a sustained release material into cilostazol. However, when a bulk cilostazol powder having an average particle diameter of about 20 μm is used, the resulting preparation showed a low absorbability at the lower portion of the digestive tube and the absorbability was not improved by adding a dispersing and/or solubilizing agent.

DISCLOSURE OF INVENTION

The present inventors have invented the preparation capable of remarkably increasing absorption of cilostazol even at the lower portion of the digestive tract, by incorporating a dispersing and/or solubilizing agent to a fine powder of cilostazol according to a simple apparatus and an easy operation without adjusting the powder to average particle size of less than about 400 nm.

One of objects of the present invention is to provide a novel preparation wherein absorption of cilostazol even at the lower portion of the digestive tract is improved.

Further, another object of the present invention is to provide a method of improving absorbability of a slightly soluble drug such as cilostazol, which is hard to be absorbed at the lower portion of the digestive tract.

Further, another object of the present invention is to provide a sustained release preparation of cilostazol, which contains a cilostazol preparation capable of releasing cilostazol even at the lower portion of the digestive tract.

In the present invention, the upper portion of the digestive tract is a digestive organ exemplified by stomach or small intestine and the like, and the lower portion of the digestive tract is a digestive organ exemplified by large intestine and the like.

If cilostazol can be absorbed widely ranging from small intestine to large intestine at the lower portion of the digestive tract, it can be absorbed for a long time by a single oral administration. Therefore, blood concentration capable of continuously exerting a desired drug efficacy can be obtained and it becomes possible to suppress the above unfavorable side effects such as headache.

The present inventors have intensively studied to obtain a preparation capable of accelerating absorption of cilostazol at the lower portion of the digestive tract. As a result, they have found that the absorption is drastically improved by forming cilostazol as an active ingredient into a fine powder and further improving the dispersibility and/or solubility of the fine powder. More specifically, they have found that the absorption from the lower portion of the digestive tract can be drastically improved by adding a dispersing and/or a solubilizing agent thereby to improve the dispersibility and/or solubility of the fine cilostazol powder in comparison with the case where a bulk or fine powder of cilostazol is used alone or the bulk cilostazol powder is merely mixed with a dispersing and/or solubilizing agent. Thus, the present invention has been completed.

Thus, the present invention relates to the following inventions:

1. A cilostazol preparation having a capability of dissolving cilostazol even at the lower portion of the digestive tract, which comprises incorporating a fine powder of cilostazol as an active ingredient into a dispersing and/or solubilizing agent.

2. The cilostazol preparation according to the item 1, wherein said dispersing and/or solubilizing agent is selected from the group consisting of a water-soluble polymer, a surfactant and a mixture thereof.

3. The cilostazol preparation according to the item 2, wherein said fine powder of cilostazol is a fine powder having average particle diameter of about 10 µm or less.

4. The cilostazol preparation according to the item 3, wherein said dispersing and/or solubilizing agent is incorporated within a range from 0.005 to 50 parts by weight based on 1 part by weight of cilostazol.

5. The cilostazol preparation according to the item 3 or 4, wherein said dispersing and/or solubilizing agent is selected from the group consisting of a water-soluble polymer, a surfactant and a mixture thereof.

6. The cilostazol preparation according to the item 5, wherein said dispersing and/or solubilizing agent is a surfactant.

7. The cilostazol preparation according to the item 6, wherein said surfactant is an alkyl sulfate salt.

8. The cilostazol preparation according to the item 5, wherein said fine powder of cilostazol is a fine powder having average particle diameter of about 7 µm or less.

9. The cilostazol preparation according to the item 8, wherein said dispersing and/or solubilizing agent is incorporated within a range from 0.01 to 10 parts by weight based on 1 part by weight of cilostazol.

10. The cilostazol preparation according to the item 8, wherein said fine powder of cilostazol is a fine powder having average particle diameter of about 5 µm or less.

11. The cilostazol preparation according to the item 8, wherein said dispersing and/or solubilizing agent is a surfactant.

12. The cilostazol preparation according to the item 11, wherein said fine powder of cilostazol is a fine powder having average particle diameter of about 5 µm or less.

13. The cilostazol preparation according to the item 12, wherein said surfactant is an alkyl sulfate salt.

14. The cilostazol preparation according to the item 13, wherein said alkyl sulfate salt is a sodium lauryl sulfate.

15. A process for improving absorbability of a slightly soluble drug which is hard to be absorbed at the lower portion of the digestive tract, which comprises forming said slightly soluble drug as an active ingredient into a fine powder and improving dispersibility and/or solubility of said slightly soluble drug.

16. The process for improving the absorbability at the lower portion of the digestive tract according to the item 15, wherein a dispersing and/or solubilizing agent is incorporated into said slightly soluble drug thereby to improve the dispersibility and/or solubility of said slightly soluble drug.

17. The process for improving the absorbability at the lower portion of the digestive tract according to the item 15, wherein said slightly soluble drug as an active ingredient is cilostazol.

18. The process for improving the absorbability at the lower portion of the digestive tract according to the item 17, wherein a dispersing and/or solubilizing agent is incorporated into said slightly soluble drug thereby to improve the dispersibility and/or solubility of said slightly soluble drug.

19. The process for improving the absorbability at the lower portion of the digestive tract according to the item 17, wherein said fine powder of cilostazol is a fine powder having average particle diameter of about 10 µm or less.

20. A sustained release preparation of cilostazol which contains any one of cilostazol preparations described in the items 1 to 14.

21. The sustained release preparation according to the item 20, which has a capability of releasing cilostazol even at the lower portion of the digestive tract.

22. The sustained release preparation according to the item 21, wherein the cilostazol preparation is coated with a sustained release material.

23. The sustained release preparation according to the item 21, which is a dry coated tablet comprising a sustained release outer layer portion containing cilostazol, and a sustained release core tablet containing a cilostazol preparation, wherein a solubility of said core tablet is more rapid than that of said outer layer portion.

24. The sustained release preparation according to the item 21, which is a tablet containing core granules wherein sustained release core granules containing a cilostazol preparation are coated with an enteric material and further said sustained release core granules are compressed with an outer layer portion containing cilostazol.

25. The sustained release preparation according to the item 21, which is a capsule comprising granules coated with an enteric material wherein said granules contain a cilostazol preparation and rapid release powders or tablets containing cilostazol.

26. The sustained release preparation according to the item 21, which is a multiple-unit type preparation wherein at least more than 2 of sustained release small tablets containing a cilostazol preparation are contained.

27. A fine powder of cilostazol having average particle diameter of about 10 µm or less, which is for a starting material of a sustained release preparation of cilostazol.

28. The fine powder of cilostazol according to the item 27, which has an average particle diameter of about 5 µm or less.

In the present invention, "a dispersing and/or solubilizing agent" is an agent capable of suspending, emulsifying or dissolving a slightly water-soluble drug in water.

In the present invention, "a cilostazol preparation" is a preparation which comprises incorporating at least a fine powder of cilostazol into a dispersing and/or solubilizing agent, which is capable of dissolving cilostazol even at the lower portion of the digestive tract.

In the present invention, "a sustained release preparation" is a preparation which shows a sustained release when orally administered.

BEST MODE FOR CARRYING OUT THE INVENTION

Figure 1:
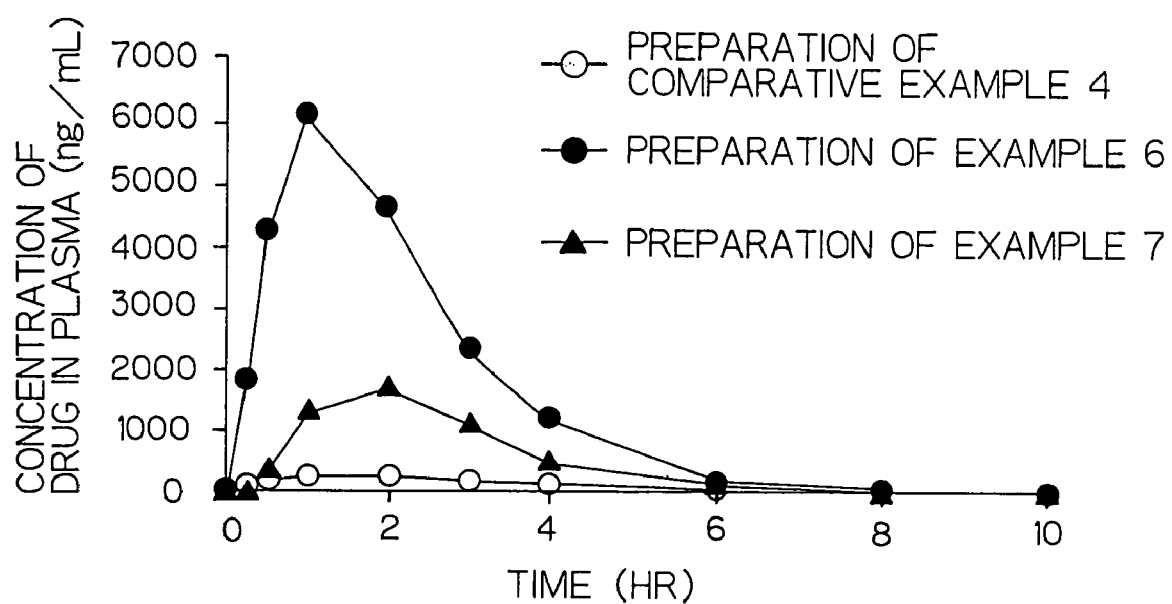
FIG. 1 is a graph showing a change in concentration of a drug in plasma after preparations of Example 6, Example 7 and Comparative Example 4 were orally administered to beagle dogs under fasting.

The desired preparation wherein the absorbability of cilostazol is improved according to the present invention can be obtained by forming cilostazol as an active ingredient into a fine powder and further incorporating a dispersing and/or solubilizing agent thereby to improve the dispersibility and/or the solubility of the fine cilostazol powder. To improve the dispersibility and/or solubility of the cilostazol fine powder, cilostazol and a dispersing and/or solubilizing agent are mixed and finely pulverized, a fine cilostazol powder and a dispersing and/or solubilizing agent are subjected to wet granulation, a cilostazol fine powder is dispersed in a solution of dispersing and/or solubilizing agent and then the resulting dispersion is formed into fine granules or granules by spray drying or freeze-drying, or the resulting dispersion is formed into tablets by compression forming.

The cilostazol preparation of the present invention is obtained by mixing a fine cilostazol powder and a dispersing and/or solubilizing agent with a conventional carrier and forming the mixture into a powder, fine granule, granule, pill, tablet, or capsule.

As the carrier, there can be widely used those which have been conventionally known in this field. Examples thereof include excipients such as lactose, D-mannitol, sucrose, sodium chloride, glucose, starch, calcium carbonate, kaolin, crystalline cellulose, low substituted hydroxypropylcellulose, hydroxypropylmethylcellulose acetate succinate, and cilicate; binders such as water, ethanol, propanol, simple syrup, glucose solution, starch solution, gelatin solution, sodium carboxymethylcellulose, shellac, methylcellulose, hydroxypropylcellulose, hydroxypropylmethylcellulose, polyvinyl alcohol, and polyvinyl pyrrolidone; disintegrators such as dry starch, agar powder, calcium carboxymethylcellulose, sodium hydrogencarbonate, calcium carbonate, polyoxyethylene sorbitan fatty acid esters, monoglyceride stearate, starch, low substituted hydroxypropylcellulose, sodium carboxymethylstarch, and croscarmellose sodium; lubricants such as purified talc, stearate salt, powdered boric acid, polyethylene glycol, colloidal silicic acid, and hardened oil; and plasticizers such as glycerin fatty acid ester, dioctyl phthalate, dibutyl phthalate, triacetin, polysorbate 80, triethyl citrate, and castor oil. These carriers can be appropriately selected and used.

In addition to the fine cilostazol powder as the active ingredient, a dispersing and/or solubilizing agent can be incorporated into the preparation of the present invention, thereby to enhance the dispersion and/or the dissolution absorbability of the fine cilostazol powder, particularly absorbability at the lower portion of the digestive tract.

The usable dispersing and/or solubilizing agent includes, for example, water-soluble polymers such as polyvinyl alcohol, polyvinyl pyrrolidone, hydroxypropylcellulose, hydroxypropylmethylcellulose, carboxymethylcellulose, and polyacrylic acid; and surfactants such as sodium lauryl sulfate and decaglyceryl monolaurate. Surfactants are preferred.

These dispersing and/or solubilizing agent can be used alone or in combination.

The surfactant used in the present invention includes ionic and nonionic surfactants, for example, polyglycerin fatty acid ester such as decaglyceryl monolaurate and decaglyceryl monomyristate; polyoxyethylene sorbitan fatty acid ester such as polyoxyethylene sorbitan monooleate; polyethylene glycol fatty acid ester such as polyoxyethylene monostearate; polyoxyethylene alkyl ether such as polyoxyethylene lauryl ether; polyoxyethylene castor oil and hardened castor oil, such as polyoxyethylene hardened castor oil; sucrose ester of fatty acid such as sucrose stearate ester and sucrose palmitate ester; and alkyl sulfate salt such as sodium lauryl sulfate and magnesium lauryl sulfate. These surfactants can be used alone or in combination.

As the surfactant used as the dispersing and/or solubilizing agent in the present invention, alkyl sulfate salt is preferred and lauryl sulfate salt is more preferred, and sodium lauryl sulfate is most preferred.

The cilostazol preparation of the present invention characterized in that the dispersibility and/or the solubility of a fine cilostazol powder is improved and capable of dissolving cilostazol even at the lower portion of the digestive tract is prepared by adding a dispersing and/or solubilizing agent to cilostazol, 0.005 to 50 parts by weight, preferably 0.01 to 10 parts by weight, more preferably 0.01 to 5 parts by weight of the dispersing based on 1 part by weight of cilostazol, and 0.1 to 99 parts by weight of the other carrier may be optionally added.

In case that the addition amount of a dispersing and/or solubilizing agent is too small, it results in lowering of the absorption because of lowering dissolution rate. In opposition, the addition of too many amounts is restricted from aspects of preparation form, and toxicity such as mucous trouble or pharmaceutical affairs low depending on kinds of dispersing and/or solubilizing agents.

The dispersing and/or solubilizing agent can be added on pulverization of a bulk cilostazol powder or wet granulation of a pulverized bulk cilostazol powder, or added by dispersing the pulverized bulk cilostazol powder in a solution of the dispersing and/or solubilizing agent and spray-drying the suspension.

A dry powder can also be obtained by dissolving sugar alcohols such as D-mannitol, xylitol, and sorbitol; saccharides such as sucrose and lacrtose; water-soluble substances such as dextrin and dextran; and surfactants such as polysolbate 80, sodium lauryl sulfate and sugar ester in a suspension of cilostazol formed into microgranules by wet pulverization, and spray-drying the resulting solution by a conventional procedure.

The cilostazol preparation of the present invention can be formed into pharmaceutical preparations such as tablets, granules, fine granules, or powders. For example, tablets are prepared from a fine powder of cilostazol using a conventional carrier according to a conventional procedure. Granules or fine granules can be prepared by adding the same carrier to the fine powder of cilostazol and granulating the mixture by using a general process such as high-speed stirring granulation, fluid-bed granulation, stirring fluid-bed granulation, centrifuging flow granulation, or extrusion granulation. Furthermore, powders are prepared by mixing the fine powder of cilostazol with the carrier such as excipient by using conventional procedure, or by a process such as fluid-bed granulation, stirring fluid-bed granulation or extrusion granulation.

In the cilostazol preparation according to the present invention, the average particle diameter of the fine cilostazol powder to be used is usually about 10 μm or less, preferably about 7 μm or less, more preferably about 5 μm or less, and most preferably about less than 4 μm. The fine cilostazol powder can be obtained according to conventional methods using various equipment, for examples, methods described in U.S. Pat. No. 5,145,684 or Japanese Laid-open Patent Publication No. 7-291869, etc. For that purpose, any equipment may be used as far as the desired particle diameter can be attained, and examples thereof include jet mil, hammer mill, rotary ball mill, vibration ball mill, shaker mill, rod mill, and tube mill. When using a ball mill or a beads mill, any of dry pulverization or wet pulverization may be conducted.

Describing in detail, pulverization using a jet mill can be carried out, for example, by spraying a compressed air at about 6 kg/cm$^2$ thereby causing collision between a raw crystal and a ceramic collision plate, or by collision between granules, and classifying and recovering the resulting fine powder using a cyclone adjusted previously to a predetermined clearance.

Process for improving the dispersibility of the fine cilostazol powder includes, for example, process for adding a dispersing as described above, and mixing with a carrier and pulverization, kneading with an excipient, flow, stirring flow and melt granulations, and spray drying or freeze-drying after forming into a suspension, or mixing with a carrier for a long time. Process for improving the dispersibility of the fine cilostazol sometimes accords to process for improving the solubility of the same.

The cilostazol preparation according to the present invention, which is capable of dissolving cilostazol even at the lower portion of the digestive tract, can also be formed into a sustained release preparation of the present invention by sustained release coating. That is, the sustained release preparation is obtained by coating cilostazol-containing fine granules, granules, pills or tablets with a sustained release coating material.

The sustained release coating material includes, for example, enteric materials such as cellulose acetate terephthalate, hydroxypropylmethylcellulose acetate succinate, hydroxypropylmethylcellulose phthalate, and methacrylic acid copolymer; and insoluble materials such as ethylcellulose and waxes. Plasticizers such as these materials, triethyl citrate, monoglyceride and polyethylene glycol; and usually incorporated additives such as talc and titanium oxide can be selected and used.

A sustained release preparation can also be obtained by preparing a hydrogel type matrix using a high-viscosity water-soluble polymer as a sustained release material, or preparing a matrix with a water-insoluble material such as wax, but a mechanism of forming into a sustained release preparation is not limited thereto. Preferred sustained release preparation is a sustained release preparation having a capability of releasing cilostazol even at the lower portion of the digestive tract.

As a preferred aspect of the sustained release preparation of the present invention, there can be provided a sustained release preparation in the form of a dry coated tablet, comprising the above cilostazol preparation having a capability of releasing cilostazol even at the lower portion of the digestive tract in a sustained release core portion having a larger dissolution rate than that of the outer layer portion, and a sustained release cilostazol in the outer layer portion.

As another preferred aspect, there can be provided a sustained release preparation in the form of a granule-containing tablet, which is obtained by coating core granules containing the above cilostazol preparation having a capability of releasing cilostazol even at the lower portion of the digestive tract with an enteric material, and compressing the coated core granules with an outer layer containing cilostazol.

As another preferred aspect, there can be provided a sustained release preparation in the form of a capsule, which contains a sustained release granule obtained by coating core granules containing the above cilostazol preparation having a capability of releasing cilostazol even at the lower portion of the digestive tract with an enteric material and a rapid release powder or tablet containing cilostazol.

As another preferred aspect, there can be provided a sustained release preparation, which contains a sustained release preparation having a capability of releasing cilostazol even at the lower portion of the digestive tract and at least one or more of a substance capable of swelling in water and/or a water-soluble substance capable of inducing osmotic pressure which are surrounded by semipermeable membrane having water permeability but substantially possessing no permeability of said water-swelling substance and/or said osmotic pressure inducing substance.

As still another aspect, there can be provided a multiple-unit type sustained release preparation comprising at least two small tablets containing the above cilostazol preparation having a capability of releasing cilostazol even at the lower portion of the digestive tract according to the present invention.

More specifically, a dry coated tablet is a sustained release preparation obtained by coating a core tablet, which is obtained by compressing a mixture of a fine cilostazol powder, a dispersing and/or solubilizing agent such as surfactant, a small amount of a hydrophilic gel-forming polymer, and a usually used carrier such as disintegrator according to a conventional procedure, with granules for compressing an outer layer portion, comprising cilostazol, a hydrophilic gel-forming polymer, and a usually used carrier such as lactose.

The core tablet having a capability of releasing cilostazol at the lower portion of the digestive tract preferably contains the above cilostazol preparation having a capability of releasing cilostazol even at the lower portion of the digestive tract according to the present invention, a small amount of a hydrophilic gel-forming polymer and a disintegrator in view of the dispersibility and/or solubility and sustained release at the lower portion of the digestive tract.

After the dry coated tablet is orally administered, the outer layer forms a hydrophilic gel, thereby to slowly release cilostazol and deliver the core tablet to the lower portion of the digestive tract while avoiding erosion of the core tablet. At the lower portion of the digestive tract where the amount of water is small and enterokinesis is not positive, the core tablet sufficiently disperse and/or dissolve and release a fine cilostazol powder with an aid of the above dispersing and/or solubilizing agent while slowly releasing cilostazol with an aid of a hydrophilic gel.

The hydrophilic gel-forming polymer includes, for example, hydrophilic polymers such as hydroxypropylcellulose, hydroxypropylmethylcellulose, polyvinyl pyrrolidone, methylcellulose, and polyethylene oxide; and polymer saccharides such as carrageenan, guar gum and arabic gum;

and these hydrophilic gel-forming polymers can be used alone or in combination. Among these hydrophilic gel-forming polymers, hydroxypropylcellulose, hydroxypropylmethylcellulose and polyethylene oxide are preferred, and hydroxypropylmethylcellulose is particularly preferred.

The disintegrator includes, for example, low substituted hydroxypropylcellulose, croscarmellose sodium, cross povidone, and carboxymethyl starch. Among these disintegrators, low substituted hydroxypropylcellulose and croscarmellose sodium are preferred, and low substituted hydroxypropylcellulose is particularly preferred.

The amount of cilostazol to be incorporated into the nulcear tablet is within a range from 10 to 95%, preferably from 20 to 90%, and more preferably from 30 to 80%, based on the amount of cilostazol of the whole dry coated tablet.

The amount of the hydrophilic gel-forming polymer to be incorporated into the core tablet is within a range from 1 to 50%, preferably from 2 to 45%, and more preferably from 3 to 40%, based on the amount of cilostazol of the core tablet.

If necessary, the core tablet may be coated with a usually used enteric polymer or water-soluble polymer.

The outer layer requires enough thickness to avoid erosion of the core tablet, and the thickness is not less than 1 mm, preferably not less than 1.5 mm, and more preferably from 1.5 to 3 mm, at one side.

The amount of the hydrophilic gel-forming polymer to be incorporated into the outer layer is within a range from 5 to 80%, preferably from 10 to 70%, and more preferably from 10 to 60%, based on the whole outer layer. When using hydroxypropylmethylcellulose as the hydrophilic gel-forming polymer, the amount is from 5 to 80%, preferably from 7 to 70%, and more preferably from 10 to 65%.

More specifically, a granule-containing tablet is a sustained release preparation obtained by coating core granules comprising a fine cilostazol powder, a dispersing and/or solubilizing agent such as surfactant, and a usually used carrier with an enteric material and a usually used carrier to form coated granules, and coating the coated granules with an outer layer portion, comprising cilostazol, a hydrophilic gel-forming polymer, and a usually used carrier such as lactose.

The coating granules having a capability of releasing cilostazol at the lower portion of the digestive tract are preferably those obtained by coating, core granules comprising the above cilostazol preparation having a capability of releasing cilostazol even at the lower portion of the digestive tract according to the present invention, and an excipient which mainly dissolves in large intestine, with an enteric material which mainly dissolves in intestines in view of the dispersibility and/or solubility and sustained release at the lower portion of the digestive tract.

After the granule-containing tablet is orally administered, the outer layer forms a hydrophilic gel, thereby to slowly release cilostazol, and also moves in the digestive tract while releasing coated granules. The core granules are delivered to the lower portion of the digestive tract, and cilostazol begins to dissolve when the pH value increases. At the lower portion of the digestive tract where the amount of water is small and enterokinesis is not positive, the core granules sufficiently disperse and/or dissolve and release a fine cilostazol powder with an aid of the above dispersing and/or solubilizing agent.

The excipient which dissolves in large intestine includes, for example, hydroxypropylmethylcellulose, hydroxypropylmethylcellulose phthalate, hydroxypropylmethylcellulose acetate succinate, and methacrylic acid copolymer (e.g. EUDRAGID S). Among these exipients, hydroxypropylmethylcellulose acetate succinate and methacrylic acid copolymer (e.g. EUDRAGID S) are preferred, and hydroxypropylmethylcellulose acetate succinate which is a type dissolving at a lower pH (at the pH of about 5.5) is particularly preferred.

The enteric material includes, for example, conventional enteric materials. Among these enteric materials, hydroxypropylmethylcellulose acetate succinate, cellulose acetate, hydroxypropylmethylcellulose phthalate, carboxymethylethylcellulose, methacrylic acid copolymer, and methacrylic acid copolymer L are preferred, and hydroxypropylmethylcellulose acetate succinate which is a type dissolving at the pH of about 7 is particularly preferred.

The amount of cilostazol to be incorporated into the core granules is within a range from 10 to 95%, preferably from 20 to 90%, and more preferably from 30 to 80%, based on the amount of cilostazol of the whole granule-containing tablet.

The amount of the enteric material is within a range from 10 to 200%, preferably from 20 to 100%, and more preferably from 20 to 60%, based on the core granules.

As the outer layer portion, the same granules for compressing the outer layer portion as those in the dry coated tablet can be used.

Since the granule-containing tablet is liable to be broken by impact because it contains granules, it may be coated with a usually used coating agent, if necessary.

More specifically, the capsule containing the granule coated with an enteric material is the one which contains the same coated granule as the granule coated with an enteric material in the above granule-containing tablet and, cilostazol and a rapid release powder, granule or tablet prepared from a usually used carrier such as excipient and disintegrator.

After orally administered, the coated granule-containing capsule rapidly dissolve cilostazol from the rapid release granule or the rapid release small tablet and the coated granule transfers the core granule at the lower portion of the digestive tract while spreading over the digestive tract.

The amount of cilostazol to be incorporated into the coated granule is within a range from 10 to 95%, preferably from 20 to 90%, and more preferably from 30 to 80%, based on the amount of cilostazol of the whole coated granule-containing capsule.

Any commonly used carrier can be used as the rapid release portion for containing cilostazol.

In addition, a superior sustained release preparation can be prepared by incorporating an organic acid such as citric acid into the enteric material-containing granule which is contained in the above granule-containing tablet and the above coated granule-containing capsule.

When sodium chloride is incorporated into the core granule for improving solubility of hydroxylpropylmethylcellulose acetate succinate, it is the problem that the granule strength is weakened in process of extrusion granulation. The addition of organic acid prevents from the above problem. The addition of organic acid to the enteric material film improves to be resistant to alkali.

More specifically, a multiple-unit type sustained release preparation is a sustained release preparation containing two or more sustained release small tablets comprising a fine cilostazol powder, a dispersing and/or solubilizing agent such as surfactant, a hydrophilic gel-forming polymer, and a usually used carrier such as lactose.

After the multiple-unit type sustained release preparation is orally administered, plural sustained release small tablets are released from the capsule at an arbitrary dissolution rate. Each sustained release small tablet forms a hydrophilic gel with a proper time lag and moves to the lower portion of the digestive tract while slowly releasing cilostazol. At the lower portion of the digestive tract where the amount of water is small and enterokinesis is not positive, the sustained release small tablets sufficiently disperse and/or dissolve and release a fine cilostazol powder with an aid of the above dispersing and/or the above solubilizing agent.

The hydrophilic gel-forming polymer includes, for example, the above-described hydrophilic gel-forming polymers. Among these hydrophilic gel-forming polymers, hydroxypropylmethylcellulose is particularly preferred. The amount of the hydrophilic gel-forming polymer is within a range from 10 to 90%, preferably from 20 to 80%, and more preferably from 25 to 75%, based on the whole sustained release small tablet.

When using hydroxypropylmethylcellulose, any commercially available one is used, but those having high viscosity are preferred. The viscosity at 20° C. of an aqueous 2% solution is not less than 400 cps, and preferably from 400 to 200,000 cps.

The sustained release small tablet has a diameter within a range from about 2 to 7 mm, and preferably from about 4 to 6.5 mm. The number of the sustained release small tablets with which a capsule is packed is usually not less than 2, preferably from 2 to 20, and more preferably from 3 to 10.

The multiple-unit type sustained release preparation further may contain a rapid released granule or a rapid release small tablet which is prepared from cilostazol and a usually used carrier such as excipient and disintegrator.

The above respective aspects of the sustained release preparation are intended to illustrate the sustained release preparation having a capability of releasing cilostazol even at the lower portion of the digestive tract, but are not to be construed to limit the scope of the sustained release preparation of the present invention.

The dose of cilostazol as the active ingredient in the preparation of the present invention varies depending on the age, sex, body weight, and conditions of the patient, but is usually within a range from 50 to 300 mg, preferably from 50 to 250 mg, and more preferably from 100 to 250 mg per day. The preparation of the present invention preferably contains cilostazol in the amount within the above range per unit dose to attain a desired effect by administering one time per day.

EXAMPLES

The following Comparative Examples, Examples and Test Examples further illustrate the preparation of the present invention and effect in more detail.

Comparative Example 1

Bulk cilostazol powder having an average particle diameter of about 20 μm.

Comparative Example 2

100 g of a bulk cilostazol (CLZ) powder having an average particle diameter of about 20 μm and 10 g of sodium lauryl sulfate (SLS) were weighed, charged in a polyethylene bag, and then mixed with shaking.

Example 1

100 g of a bulk cilostazol (CLZ) powder having an average particle diameter of about 20 μm and 10 g of sodium lauryl sulfate (SLS) are mixed in a polyethylene bag, and then pulverized by using a jet mill (100AS, manufactured by POWREK Co.) to obtain a cilostazol powdered preparation having an average particle diameter of about 3 μm.

Example 2

300 g of a bulk cilostazol (CLZ) powder having an average particle diameter of about 3 μm pulverized by using a jet mill and 132 g of D-mannitol are mixed and then charged in a fluid-bed granulator (NQ-160, manufactured by Fuji Paudal Co., Ltd.). The mixture is subjected to wet granulation by spraying 400 g of an aqueous solution containing 7.5% sodium lauryl sulfate (SLS) and 4.5% hydroxypropylcellulose (trade name: HPC-SL)(corresponding to a solid of 30 g for SLS and 18 g for HPC), and then dried to obtain a cilostazol powdered preparation.

Example 3

To the powder obtained in Example 2, 1.25% magnesium stearate is added and the mixture was compressed so that one tablet has a weight of 162 mg using a single punch tableting machine (No. 2B, manufactured by KIKUSUI SEISAKUSHO Co.) equipped with a punch having a diameter of 8 mm to obtain tablets containing cilostazol in the amount of 100 mg per tablet.

Example 4

3.3 g of polyvinyl alcohol (PVA), 10 g of D-mannitol and 2 g of sodium lauryl sulfate (SLS) are dissolved in 106 g of water. After 20 g of a bulk cilostazol (CLZ) powder having an average particle diameter of about 3 μm pulverized by using a jet mill is dispersed, this solution is spray-dried to obtain a cilostazol powdered preparation.

Example 5

300 g of a bulk cilostazol (CLZ) powder having an average particle diameter of about 3 μm pulverized by using a jet mill and 162 g of D-mannitol are mixed and then charged in a fluid-bed granulator (NQ-160, manufactured by FUJI POWDAL Co., Ltd.). The mixture is subjected to wet granulation by spraying 400 g (corresponding to a solid of 18 g for HPC) of an aqueous solution containing 4.5% hydroxypropylcellulose (trade name: HPC-SL), and then dried to obtain a cilostazol powdered preparation.

Comparative Example 3

100 g of cilostazol having an average particle diameter of about 20 μm is mixed with 30 g of corn starch, 25 g of crystalline cellulose and 12 g of carboxymethylcellulose calcium. After an aqueous solution containing 1.5 g of hydroxypropylmethylcellulose is added, the mixture is granulated with kneading and sieved to form granules for compression. Then, 1.5 g of magnesium stearate as a lubricant is added and the granules are compressed so that one tablet has a weight of 170 mg using a punch having a diameter of 8 mm to obtain tablets containing cilostazol in the amount of 100 mg per tablet.

Example 6

200 g of cilostazol having an average particle diameter of about 20 μm and 50 g of polyvinyl alcohol (203, manufactured by KURARAY Co., Ltd.) are dispersed and dissolved in 750 g of water, and then pulverized, together with 4000 g of zirconia beads having a diameter of 0.3 mm, in DYNO-MILL having a volume of 1.4 L (manufactured by CIMMAL ENTERPRISES Co.) at 2500 rpm for one hour to obtain a pulverized suspension of cilostazol having an average particle diameter of about 270 nm. This pulverized suspension is suitably diluted to give a 0.25% cilostazol suspension. The average particle diameter of cilostazol is measured by a dynamic light scattering process using an electrophoretic light scattering photometer (ELS-800, manufactured by OTSUKA ELECTRONICS, CO., LTD.).

Example 7

5 g of polysolbate 80 and 25 g of D-mannitol are dissolved in 100 g of the pulverized suspension obtained in Example 6 and 75 g of water is added, and then the mixture is spray-dried by using a spray dryer manufactured by NIRO Co.) under the conditions of an inlet temperature of 200° C., an outlet temperature of 110° C., an atomizer revolution of about 25000 rpm and a liquid rate of 20 g/minute to obtain a powder. Gelatin capsules are packed with 240 mg (corresponding to 100 mg for cilostazol) of this powder to obtain capsules of cilostazol.

Comparative Example 4

A bulk cilostazol powder having an average particle diameter of about 20 μm is suspended in a 0.25% polyvinyl alcohol solution to obtain a 0.25% cilostazol suspension.

Example 8

80 g of a bulk cilostazol powder having an average particle diameter of about 2 μm pulverized by using a jet mill, 20 g of hydroxypropylcellulose, 15 g of low substituted hydroxypropylcellulose (trade name: LH-31) and 15 g of sodium lauryl sulfate as a dispersing and/or solubilizing agent are mixed. After 55 g of an aqueous solution containing 2.75 g of hydroxypropylcellulose (trade name: HPC-L) as a binding solution is added, the mixture is granulated with high sheared mixer, dried and sieved to form granules. Then, 0.3 g of magnesium stearate as a lubricant is added and the granules are compressed so that one tablet has a weight of 133 mg using a punch having a diameter of 7 mm to obtain core tablets containing cilostazol in the amount of 80 mg per tablet.

Separately, 120 g of a bulk cilostazol powder having an average particle diameter of about 2 μm, 80 g of hydroxypropylmethylcellulose, 27 g of hydroxypropylcellulose (trade name: HPC-H) and 270 g of lactose are mixed, granulated with 150 g of purified water, dried and sieved to obtain granules, and then 3.0 g of magnesium stearate is added and mixed. 500 mg of granules for compressing an outer layer portion contain 120 mg of cilostazol.

Core tablets and 500 mg of granules for compressing an outer layer portion are mixed and then compressed by using a punch having a diameter of 11 mm so that one tablet has a weight of 633 mg to obtain dry coated sustain released tablets containing cilostazol in the amount of 200 mg per tablet.

Example 9

In the same manner as in Example 8, except for using 140 g of hydroxypropylmethylcellulose and 210 g of lactose as a granule for compressing an outer layer portion, sustained release dry coated tablets are obtained.

Example 10

400 g of a bulk cilostazol powder having an average particle diameter of about 2 μm pulverized by using a Jet mill, 160 g of hydroxypropylmethylcellulose acetate succinate (trade name: SHINETSU AQOAT AS-LF), 40 g of hydroxypropylmethylcellulose as a binder and 40 g of sodium lauryl sulfate as a dispersing and/or solubilizing agent are charged in a kneader (NSK-150, manufactured by OKADA SEIKO Co., Ltd.) and mixed, and then a proper amount of an aqueous solution containing 20 g of sodium chloride, 20 g of citric acid and 20 g of polysolbate 80 is added to obtain a blend. The blend is taken out, granulated by extruding using an extrusion granulator (DOMEGRAN DG-L1, manufactured by Fuji Paudal Co., Ltd.) equipped with a dome die having holes of 0.8 mm in diameter and then formed into spherical granules using a spheronization granulator (MARUMERIZER QJ-400, manufactured by Fuji Paudal Co., Ltd.). The resulting granules are dried and those having a particle diameter of 710 to 1000 μm are selected and used as core granules for coating. 750 g of a coating solution containing 7.0% hydroxypropylmethylcellulose acetate succinate (trade name: SHINETSU AQOAT AS-HF), 3.5% talc, 2.8% triethyl citrate, 0.21% sodium lauryl sulfate and 0.21% citric acid is sprayed over 600 g of core granules using a rotating flow coater (NEW MARUMERIZER NQ-160, manufactured by Fuji Paudal Co., Ltd.), followed by drying to obtain coated granules. 280 m g of the coated granules contain 100 mg of cilostazol.

Separately, 100 g of a bulk cilostazol powder having an average particle diameter of about 2 μm pulverized by using a jet mill, 75 g of hydroxypropylmethylcellulose, 195 g of lactose and 30 g of D-mannitol are mixed, granulated while adding 110 g of purified water and then dried to obtain granules for compressing an outer layer portion. 400 mg of the granules for compressing an outer layer portion contain 100 mg of cilostazol.

280 mg of coated granules, 400 mg of granules for compressing an outer layer portion and 4 mg of magnesium stearate are mixed and then compressed by using a punch having a diameter of 11 mm to obtain granule-containing sustained release tablets containing cilostazol in the amount of 200 mg per tablet.

Example 11

A coating solution containing 6% hydroxypropylmethylcellulose, 2% polyethylene glycol, 1% talc and 1% titanium dioxide is sprayed over the tablets of Example 10 to obtain coated tablets having a weight of 721.9 mg.

Example 12

In the same manner as in Example 10, except that citric acid is eliminated from the coating solution, granule-containing sustained release tablets are obtained. In the same manner as in Example 11, coated tablets are obtained.

Example 13

800 g of a bulk cilostazol powder having an average particle diameter of about 2 μm pulverized by using a jet mill, 1066 g of hydroxypropylmethylcellulose and 60 g of sodium lauryl sulfate as a dispersing and/or solubilizing agent are mixed. The mixture is subjected to wet granulation with adding 1000 g of purified water, dried and then sieved to form granules. After 18 g of magnesium stearate as a lubricant is added, the granules are compressed so that one tablet has a weight of 97.2 mg using a punch having a diameter of 6.5 mm to obtain sustained release small tablets containing cilostazol in the amount of 40 mg per tablet.

Capsules are packed with the resulting sustained release small tablets so that one capsule contains five tablets to obtain a multiple unit type sustained release preparation containing cilostazol in the amount of 200 mg per capsule.

Example 14

800 g of a bulk cilostazol powder having an average particle diameter of about 2 μm pulverized by using a jet mill, 800 g of hydroxypropylmethylcellulose, 284 g of D-mannitol and 60 g of sodium lauryl sulfate as a dispersing and/or solubilizing agent are mixed. The mixture is subjected to wet granulation while adding 900 g of purified water, dried and then sieved to form granules. After 16 g of magnesium stearate as a lubricant is added, the granules are compressed so that one tablet has a weight of 98.0 mg using a punch having a diameter of 6.5 mm to obtain sustained release small tablets containing cilostazol in the amount of 40 mg per tablet.

Capsules are packed with the resulting sustained release small tablets so that one capsule contains five tablets to obtain a multiple unit type sustained release preparation containing cilostazol in the amount of 200 mg per capsule.

Example 15

In the same manner as in Example 14, except that 500 g of hydroxypropylmethylcellulose and 584 g of D-mannitol are used and sodium lauryl sulfate is not added, sustained release small tablets which has higher dissolution rate than those described in previous Examples 13, 14, having a weight of 95.0 mg per tablet and comprising cilostazol in the amount of 40 mg per tablet, are obtained.

Capsules are packed with the resulting sustained release small tablets so that one capsule contains two sustained release small tablets having higher dissolution rate and three sustained release small tablets obtained in Example 13 or Example 14 to obtain a multiple unit type sustained release preparation containing cilostazol in the amount of 200 mg per capsule.

Example 16

Capsules are packed with tablets so that one capsule contains one sustained release tablet having a higher dissolution rate obtained in Example 15 and four sustained release small tablets obtained in Example 13 or Example 14 to obtain a multiple-unit type sustained release preparation containing cilostazol in the amount of 200 mg per capsule.

Example 17

800 g of cilostazol, 280 g of corn starch, 200 g of crystalline cellulose and 128 g of carmellose calcium are mixed and an aqueous solution containing 16 g of hydroxypropylcellulose as a binder is added. The mixture is subjected to wet granulation, dried and sieved to form granules. Then, 16 g of magnesium stearate as a lubricant is added and the granules are compressed so that one tablet has a weight of 72.0 mg using a punch having a diameter of 5.5 mm to obtain immediate release small tablets containing cilostazol in the amount of 40 mg per tablet.

Capsules are packed with tablets so that one capsule contains the resulting one immediate release small tablet and four sustained release small tablets obtained in Example 13 or Example 14 to obtain a multiple-unit type sustained release preparation containing cilostazol in the amount of 200 mg per capsule.

Example 18

In the same manner as in Example 13, except for using 200 g of sodium lauryl sulfate and 20 g of magnesium stearate, sustained release small tablets containing cilostazol in the amount of 40 mg per capsule are obtained.

Capsules are packed with tablets so that one capsule contains the resulting five sustained release small tablets to obtain a multiple unit type sustained release preparation containing cilostazol in the amount of 200 mg per capsule.

Example 19

150 g of a bulk cilostazol powder having an average particle diameter of about 2 μm pulverized by using a jet mill is mixed with 60 g of hydroxypropylmethylcellulose acetate succinate (SHINETSU AQOAT AS-LF, manufactured by SHINETSU Chemical industries, Co., Ltd.), 15 g of hydroxypropylmethylcellulose (METOLOSE 90SH400, manufactured by SHINETSU Chemical industries, Co., Ltd.) and 12.5 g of sodium lauryl sulfate. After the resulting mixed powder is charged in a kneader, an aqueous solution containing sodium chloride, citric acid and polysolbate 80 (each 7.5 g) is added and purified water is further added to obtain a proper blend. This blend is subjected to extrusion granulation using an extrusion granulator equipped with a dome die having holes of 0.8 mm in diameter and then formed into spherical granules using a spheronization granulator. The above operation was repeated six times, and then the resulting granules are dried and those having a particle diameter of 710 to 1000 μm are selected and used as core granules for coating. 150 mg of cilostazol is contained in 260 mg of the core granules.

Separately, 160 g of triethyl citrate, 12 g of sodium lauryl sulfate and 13 g of citric acid are dissolved in 5215 g of purified water and then 400 g of hydroxypropylmethylcellulose acetate succinate (SHINETSU AQOAT AS-HF) and 200 g of talc are dispersed in the resulting solution to prepare a coating solution. After weighing 1040 g of core granules for coating, 4800 to 5300 g of the coating solution is sprayed using a rotating flow coating machine to obtain coated granules. The coating operation is terminated at the time when 417 mg of coated granules contain 150 mg of cilostazol, followed by drying with heating.

Separately, 500 g of a bulk cilostazol powder having an average particle diameter of about 2 μm pulverized by using a jet mill is mixed with 100 g of crystalline cellulose, 100 g of corn starch, 50 g of carmellose calcium and 15 g of hydroxypropylcellulose after weighing them. The mixture is charged in a kneader and a proper quantity of purified water as a binding solution is added, followed by high sheared granulation. The resulting granules are dried over a fluid-bed and sieved to form granules, and then 5 g of magnesium stearate as a lubricant is added. The granules are compressed by using a punch having a diameter of 6.5 mm to obtain immediate release tablets (each 77 mg) containing cilostazol in the amount of 50 mg per tablet.

Capsules are packed with tablets so that one capsule contains sustained release coated granules containing cilostazol in the amount of 150 mg and one immediate release tablet containing cilostazol in the amount of 50 mg to obtain sustained release capsules.

Example 20

200 g of a bulk cilostazol powder having an average particle diameter of about 2 µm pulverized by using a jet mill is mixed with 40 g of crystalline cellulose, 20 g of corn starch, 40 g of carboxymethylcellulose calcium and 10 g of hydroxypropylcellulose. After the mixture is charged in a kneader, 10 g of polysolbate 80 was added and a sufficient quantity of purified water as a binding solution is added, followed by high sheared granulation. The granules are subjected to extrusion granulation using an extrusion granulator equipped with a dome die having holes of 0.8 mm in diameter and then formed into spherical granules using a spheronization granulator. The resulting granules are dried and those having a particle diameter of 710 to 1000 µm are selected to obtain immediate release granules. 80 mg of the immediate release granules contain 50 mg of cilostazol.

Capsules are packed with tablets so that one capsule contains sustained release coated granules containing cilostazol in the amount of 150 mg obtained in Example 19 and the resulting immediate release tablet containing cilostazol in the amount of 50 mg to obtain sustained release capsules.

Example 21

50 g of a bulk cilostazol powder having an average particle diameter of about 2 µm pulverized by using a jet mill is mixed with 50 g of hydroxypropylmethylcellulose (HPMC) and 200 g of lactose. The mixture is granulated with about 70 g of purified water, and then dried to obtain granules for compressing an outer layer portion. 300 mg of the resulting outer-layer granules contains 50 mg of cilostazol.

Then, about 140 mg of coated granules obtained in Example 10, 300 mg of granules for compressing an outer layer portion and 2 mg of magnesium stearate are mixed and compressed using a punch having a diameter of 10 mm to obtain granule-containing sustained release tablets containing cilostazol in the amount of 100 mg per tablet.

Examples 22 to 25

In the same manner as in Example 21, except for using granules for compressing an outer layer portion having the following composition as shown in Table 1, granules-containing sustained release tablets containing cilostazol in the amount of 100 mg per tablet.

TABLE 1

| Name of raw material | Amount (g) on granulation of granules for compressing an outer layer portion | | | |
|---|---|---|---|---|
| | Example 22 | Example 23 | Example 24 | Example 25 |
| CLZ bulk powder pulverized by using a jet mill | 50 | 50 | 50 | 50 |
| HPMC | 75 | 75 | 90 | 120 |
| Lactose | 175 | 160 | 160 | 130 |
| D-mannitol | — | 15 | — | — |

Example 26

A coating solution containing 6% hydroxypropylmethylcellulose, 2% polyethylene glycol, 1% talc and 1% titanium dioxide is sprayed over the granules-containing sustained release tablets obtained in Examples 21 to 25 to obtain coated tablets, respectively.

Example 27

Each amount of capsules obtained in Examples 19 and 20 to be packed is reduced to half to obtain preparations containing cilostazol in the amount of 100 mg per capsule.

Example 28

80 g of a bulk cilostazol powder having an average particle diameter of about 2 µm pulverized by using a jet mill, 10 g of hydroxymethylcellulose, 20 g of low substituted hydroxypropylcellulose and 15 g of sodium lauryl sulfate are mixed. After 55 g of an aqueous solution containing 3 g of hydroxypropylcellulose as a binding solution is added, the mixture is granulated with high sheared mixer, dried and sieved to form granules. Then, 0.4 g of magnesium stearate as a lubricant is added and the granules are compressed so that one tablet has a weight of 128.4 mg using a punch having a diameter of 7 mm to obtain core tablets containing cilostazol in the amount of 80 mg per tablet.

Separately, 120 g of a bulk cilostazol powder having an average particle diameter of about 2 µm, 130 g of hydroxypropylmethylcellulose and 247 g of lactose are mixed, granulated while adding 150 g of purified water, dried and sieved to obtain granules, and then 3.0 g of magnesium stearate is added and mixed. 500 mg of granules for compressing an outer layer portion contain 120 mg of cilostazol.

Core tablets and 500 mg of granules for compressing an outer layer portion are mixed and then compressed by using a punch having a diameter of 11 mm so that one tablet has a weight of 628.4 ma to obtain dry coated sustain released tablets containing cilostazol in the amount of 200 mg per tablet.

Example 29

800 g of a bulk cilostazol powder having an average particle diameter of about 3 µm pulverized by using a jet mill is mixed with 150 g of D-mannitol and 50 g of crystalline cellulose, and then the mixture is subjected to fluid-bed granulation while spraying a binding solution prepared by dissolving 15 g of hydroxypropylcellulose (HPC-SL) and 120 g of polyethylene glycol monostearate (40EO) (manufactured by Nikko Chemicals Co. under the trade name of MYS-40). After drying and addition of magnesium stearate, the granules are compressed so that one tablet has a diameter of 6.5 mm and a weight of 114 mg to obtain core tablets containing cilostazol in the amount of 80 mg per tablet.

In the same manner as in Example 28, dry coated sustain released tablets containing cilostazol in the amount of 200 mg per tablet are obtained.

Example 30

43 g of polyvinyl alcohol (manufactured by Kuraray Co., Ltd. under the trade name of PVA-203) is dissolved in 2520 g of purified water with heating, and then 434 g of cilostazol having an average particle diameter of about 20 μm is suspended in the resulting solution. Using an attritor type wet pulverizer (Dyno-Mill) packed with zirconia beads having a diameter of 0.5 mm, the suspension is pulverized at 300 rpm to obtain a pulverized suspension of cilostazol having an average particle diameter of about 250 nm.

Example 31

8 g of polysolbate 80 is dissolved in 875 g of purified water, and then 83 g of cilostazol having an average particle diameter of about 20 μm is suspended in the resulting solution. In the same manner as in Example 30, the suspension is pulverized to obtain a pulverized suspension of cilostazol having an average particle diameter of about 300 nm.

Example 32

To 300 g of the pulverized suspension obtained in Example 31, 7 g of D-mannitol and 7 g of dextrin are added, and then the mixture is spray-dried at an inlet air temperature of 200° C. to obtain a dried powder.

Example 33

39 g of poloxamer 188 (trade name: Lutrol F68) and 20 g of polysolbate 80 are dissolved in 745 g of purified water, and then 196 g of cilostazol having an average particle diameter of about 20 μm is suspended in the resulting solution. In the same manner as in Example 30, the suspension is pulverized to obtain a pulverized suspension of cilostazol having an average particle diameter of about 500 nm.

Example 34

To 300 g of the pulverized suspension obtained in Example 33, 63 g of D-mannitol is added, and then the mixture is spray-dried at an inlet air temperature of 200° C. to obtain a dried powder.

Example 35

To the pulverized suspension obtained in Example 30, D-mannitol or dextrin is added and, furthermore, polysolbate 80 and SLS is added. Then, the mixture is spray-dried at an inlet air temperature of 200° C. to obtain dried powders of the following formulation as shown in Table 2.

TABLE 2

|  | P-1 | P-2 | P-3 | P-4 | P-5 |
| --- | --- | --- | --- | --- | --- |
| CLZ | 43.4 | 43.4 | 43.4 | 43.4 | 43.4 |
| PVA | 4.3 | 4.3 | 4.3 | 4.3 | 4.3 |
| D-Mannitol | 21.7 | 21.7 | 21.7 | — | — |
| Dextrin | — | — | — | 21.7 | 21.7 |
| Polysorbate 80 | 4.3 | — | — | 4.3 | — |
| SLS | — | 4.3 | 2.2 | — | 2.2 |

Example 36

100 g of hydroxypropylcellullose is dissolved in 5000 g of purified water, and then 500 g of cilostazol having an average particle diameter of about 20 μm is suspended in the resulting solution. In the same manner as in Example 30, the suspension is pulverized to obtain a pulverized suspension of cilostazol having an average particle diameter of about 300 nm. To this pulverized suspension, D-mannitol and SLS are added, and then the mixture is spray-dried at an inlet air temperature of 200° C. to obtain a dried powder as shown in Table 3.

TABLE 3

|  | P-6 | P-7 | P-8 | P-9 | P-10 |
| --- | --- | --- | --- | --- | --- |
| CLZ | 7.58 | 22.7 | 18.9 | 18.9 | 15.2 |
| HPC-SL | 1.52 | 4.5 | 3.8 | 3.8 | 3.0 |
| D-Mannitol | — | — | — | 3.04 | 7.6 |
| SLS | — | 1.14 | 1.9 | 0.95 | 1.5 |

Example 37

100 g of cilostazol having an average particle diameter of about 20 μm and 15 g of hydroxypropylcellulose (manufactured by NIPPON SODA Co., Ltd. under the trade name of HPC-SSL) are mixed and the mixture is added to 400 g of purified water with stirring, and then cilostazol is suspended in the resulting solution. Using an attritor type wet pulverizer (Dyno-Mill) packed with 4000 g of zirconia beads having a diameter of 0.5 mm, the cilostazol suspension is pulverized to obtain a pulverized suspension of cilostazol having an average particle diameter of about 230 nm.

To this pulverized suspension, a partly pregelatinized starch (manufactured by Asahi Chemical Industry Co., Ltd. under the trade name of PCS) is added and sodium lauryl sulfate (SLS) is further added, and then the mixture is spray-dried to obtain a dry powder.

To the resulting dry powder, anhydrous dibasic calcium phosphate (manufactured by Fuji Chemical Industry Co., Ltd. under the trade name of Fujikarin), croscarmellose sodium (Ac-Di-Sol), hydroxypropylmethylcellulose (manufactured by Shietsu Chemical Industries Co., Ltd. under the trade name of METOLOSE90SH4000) and magnesium stearate (St—Mg) are added, and then the mixture is compressed to obtain core tablets having a diameter of 7 mm of the following formulation, as shown in Table 4.

TABLE 4

|  | Core tablet A | Core tablet B | Core tablet C | Core tablet D | Core tablet E | Core tablet F |
|---|---|---|---|---|---|---|
| CLZ | 80 | 80 | 80 | 80 | 80 | 80 |
| HPC-SSL | 12 | 12 | 12 | 12 | 12 | 12 |
| PCS | 24 | 24 | 24 | 24 | 24 | 24 |
| SLS | 0 | 0 | 0 | 0 | 15 | 15 |
| Fujikalin SG | 20 | 20 | 20 | 20 | 16 | 16 |
| Ac-Di-Sol | 16 | 16 | 16 | 16 | 16 | 16 |
| METOLOSE90SH4000 | — | 15 | 6 | 10 | — | 10 |
| Mgnesium stearate | 1 | 1 | 1 | 1 | 1 | 1 |
| Total (mg/Tab) | 153 | 168 | 159 | 163 | 164 | 174 |

In the same manner as in Example 28, dry coated sustained release tablets containing cilostazol in the amount of 200 mg per tablet are obtained.

Example 38

A bulk cilostazol powder having an average particle diameter of about 2 μm, hydroxypropylmethylcellulose, METOLOSE90SH4000, hydroxypropylcellulose, HPC-H, and lactose are mixed, and then the mixture is subjected to high sheared granulation while adding purified water and dried. Then, Mg stearate is added to obtain granules for compressing an outer layer portion of the following formulation, as shown in Table 5.

Using 500 mg of the resulting granules for compressing an outer layer portion and the core tablet C or D obtained in Example 37, dry coated sustained release tablets having a diameter of 11 mm, which contain cilostazol in the amount of 200 mg per tablet, are obtained.

TABLE 5

Formulation Example of Example 38

| Core tablets | Dry coated tablet P Core tablet C | Dry coated tablet Q Core tablet C | Dry coated tablet R Core tablet C | Dry coated tablet S Core tablet D | Dry coated tablet T Core tablet D | Dry coated tablet U Core tablet D |
|---|---|---|---|---|---|---|
| CLZ pulverized by using a jet mill | 120 | 120 | 120 | 120 | 120 | 120 |
| METOLOSE90SH4000 | 80 | 140 | 130 | 80 | 140 | 130 |
| HPC-H | 27 | 27 | 0 | 27 | 27 | 0 |
| Lactose | 270 | 210 | 247 | 270 | 210 | 247 |
| Mg stearate | 3 | 3 | 3 | 3 | 3 | 3 |
| Weight of outer layer (mg/Tab) | 500 | 500 | 500 | 500 | 500 | 500 |
| Weight of dry coated tablet (mg/Tab) | 659 | 659 | 659 | 663 | 663 | 663 |

Example 39

In the same manner as in Example 28, core tablets of the following formulation as shown in Table 6 are obtained, thus obtaining dry coated sustained release tablets containing cilostazol in the amount of 200 mg per tablet are obtained.

TABLE 6

| Bulk CLZ powder (average particle diameter: 2 μm) | 80 | 80 | 80 | 80 |
|---|---|---|---|---|
| HPMC | 20 | 25 | 20 | 20 |
| L-HPC (LH-31) | 15 | 20 | 10 | 20 |

TABLE 6-continued

| SLS | 15 | 5 | 20 | 10 |
|---|---|---|---|---|
| HPC-L | 2.75 | 2.75 | 2.75 | 2.75 |
| Mg stearate | 0.3 | 0.3 | 0.3 | 0.3 |
| Weight of core tablet (mg/Tab) | 133.05 | 133.05 | 133.05 | 133.05 |

Example 40

In the same manner as in Example 1 (X0), SLS is added in the following amount as shown in Table 7 to obtain cilostazol preparations having the following particle diameter.

TABLE 7

| Name of raw material | X0 | X1 | X2 | X3 | X4 | X5 |
|---|---|---|---|---|---|---|
| CLZ | 100 | 100 | 100 | 100 | 100 | 100 |
| SLS | 10 | 10 | 5 | 20 | 30 | 30 |
| Average particle diameter | 3 | 7 | 3 | 3 | 3 | 7 |

Example 41

In the same manner as in Example 10 (Y0), SLS is added in the following amount as shown in Table 8 to obtain core granules, thus obtaining granules-containing sustained release tablets.

TABLE 8

| Name of raw material | Amount (g) on granulation of granules | | | | |
|---|---|---|---|---|---|
| | Y0 | Y1 | Y2 | Y3 | Y4 |
| CLZ jet mill product | 400 | 400 | 400 | 400 | 400 |
| Average particle diameter of CLZ* | 2 | 7 | 2 | 2 | 7 |
| SLS | 40 | 40 | 20 | 80 | 80 |
| SHINETSU AQOATAS-LF** | 160 | 160 | 180 | 120 | 120 |

*μm
**Hydroxypropylmethylcellulose acetate saccinate

Example 42

In the same manner as in Example 2 (Z0), the following dispersing and solubilizing agent as shown in Table 9 are added to obtain cilostazol preparations.

TABLE 9

| Name of raw material | Z0 | Z1 | Z2 | Z3 | Z4 | Z5 |
|---|---|---|---|---|---|---|
| CLZ | 300 | 300 | 300 | 300 | 300 | 300 |
| SLS | 30 | 20 | 15 | 20 | 10 | — |
| Polysorbate 80 | — | 10 | 15 | — | 10 | 20 |
| HPC | 18 | 18 | 18 | 28 | 28 | 28 |

Cilostazol: a bulk cilostazol powder having an average particle diameter of about 3 μm Example 43

In the same manner as in Example 28, inner core tablets having a diameter of 6 mm which contain 40 mg of a bulk cilostazol powder having an average particle diameter of about 2 μm, 5 mg of sodium lauryl sulfate, 5 mg of hydroxypropylmethylcellulose, 10 mg of low substituted hydroxypropylcellulose and 0.2 mg of mangesium stearate per tablet were obtained. To the inner core tablets, an outer layer portion containing 60 mg cilostazol, 50 mg of hydroxypropylmethylcellulose, 287.5 mg of lactose and 2.5 mg of magnesium stearate were added to obtain dry coated sustained release tablets having a diameter of 10 mm, which contain 100 mg cilostazol per tablet.

Example 44

In the same manner as in Example 43 except that 100 mg of hydroxypropylmethylcellulose and 237.5 mg of lactose were contained, dry coated sustained release tablets having a diameter of 10 mm, which contain 100 mg of cilostazol per tablet, are obtained.

Example 45

In the same manner as in Example 43 except that 150 mg of hydroxypropylmethylcellulose and 187.5 mg of lactose were contained, dry coated sustained release tablets having a diameter of 10 mm, which contain 100 mg of cilostazol per tablet, are obtained.

Comparative Example 5

Bulk cilostazol powder having an average particle diameter of about 3 μm

Comparative Example 6

120 g of cilostazol powder having an average particle diameter of about 20 μm, 22.5 g of sodium lauryl sulfate, 22.5 g of L-HPC and 30 g of METOLOSE90SH4000 are mixed, and then the mixture is subjected to high-speed stirring granulation using 83 g of an aqueous 5% HPC-L solution as a binding solution and dried. Then, a lubricant is added to obtain core tablets having a diameter of 7 mm and a weight of 133 mg, which contain cilostazol in the amount of 80 mg per tablet.

Separately, 120 g of a bulk cilostazol powder having an average particle diameter of about 3 μm, 140 g of METOLOSE90SH4000, 27 g of HPC-H and 210 g of lactose are mixed, subjected to high-speed granulating while adding purified water, and then dried. 1 g of magnesium stearate is added to 165.7 g of the resulting granules to obtain granules for compressing an outer layer portion.

Core tablets and 500 mg of granules for compressing an outer layer portion are compressed by using a punch having a diameter of 11 mm to obtain dry coated sustained release tablets containing cilostazol in the amount of 200 mg per tablet.

Test Example 1

Absorption Test of Cilostazol into the Large Intestine

Preparations of Examples 1, 2, 4 and 5 and Comparative Example 1 were directly administered in a large intestine loop of female rats (3 or 4 rats per group) in the amount of 100 mg/kg calculated on the basis of cilostazol (CLZ). Then, blood was collected with a lapse of time and cilostazol concentration in blood was measured. An average cilostazol concentration in blood is shown in Table 10 and pharmacokinetic parameters after administration are shown in Table 11.

TABLE 10

Change in CLZ concentration in blood after direct administration into the large intestine of rats

| | CLZ concentration in blood (ng/mL) | | | | | |
|---|---|---|---|---|---|---|
| | 0 | 0.083 | 0.25 | 0.5 | 1.0 | 2.0* |
| Example 1 | 0 | 169 | 313 | 567 | 843 | 1066 |
| Example 2 | 0 | 227 | 394 | 575 | 1054 | 1588 |
| Example 4 | 0 | 273 | 584 | 1003 | 1702 | 2243 |
| Example 5 | 0 | 157 | 238 | 364 | 653 | 1030 |
| Comp. Example 1 | 0 | 15 | 26 | 51 | 100 | 170 |

*Time after administration (hr)

TABLE 11

CLZ pharmacokinetics parameters after direct administration into the large intestine of rats

| | $AUC_{0-2\ hr}$ (ng · hr/mL) | Cmax (ng/mL) | Tmax (hr) |
|---|---|---|---|
| Example 1 | 1464 (7.9) | 1066 (6.3) | 2.0 |
| Example 2 | 1910 (10.3) | 1588 (9.3) | 2.0 |
| Example 4 | 2930 (15.8) | 2243 (13.2) | 2.0 |
| Example 5 | 1210 (6.5) | 1030 (6.1) | 2.0 |

TABLE 11-continued

CLZ pharmacokinetics parameters after direct administration into the large intestine of rats

|  | AUC$_{0-2\,hr}$ (ng · hr/mL) | Cmax (ng/mL) | Tmax (hr) |
| --- | --- | --- | --- |
| Comp. Example 1 | 186 (1.0) | 170 (1.0) | 2.0 |

Note 1: "AUC$_{0-2\,hr}$" means an amount of cilostazol absorbed within two hours after administration, and a numeral in parenthesis denotes a magnification in case where a value of Comparative Example 1 (bulk CLZ powder alone) is 1.0.
Note 2: "C$_{max}$" means a maxium cilostazol concentration in blood, and a numeral in parenthesis denotes a magnification in case where a value of Comparative Example 1 (bulk CLZ powder alone) is 1.0.
Note 3: "T$_{max}$" means a time required to arrive at the maximum cilostazol concentration in blood.

As is apparent from the results shown in Table 10 and Table 11, high blood concentration was attained within two hours after administration in all fine powders of Examples 1, 2 and 4 prepared by incorporating a fine powder of cilostazol into sodium lauryl sulfate (SLS) and a fine powder of Example 5 prepared by incorporating HPC according to the present invention, whereas, sufficient blood concentration was not obtained in Comparative Example 1 incorporated with no SLS.

Test Example 2

Preparations of Examples 1, 2 and 4 and Comparative Example 1 were weighed in the amount of 100 mg calculated on the basis of cilostazol and subjected to a dissolution test under the following conditions. To evaluate the dissolution rate, the dissolution percentage was compared after two minutes had passed since the beginning of the test.

Conditions of Dissolution Test

Dissolution test solution: 900 mL of aqueous 0.3% sodium lauryl sulfate solution Paddle Method 75 rpm Amount of sample: amount corresponding to 100 mg of cilostazol per vessel The results are shown in Table 12.

TABLE 12

Results of cilostazol dissolution test

| Samples | Dissolution percentage after 2 minutes (%) |
| --- | --- |
| Example 1 | 96.6 |
| Example 2 | 92.5 |
| Example 4 | 83.1 |
| Comp. Example 1 | 22.7 |

As is apparent from the results of Test Example 2, the bulk powder of cilostazol of Comparative Example 1 is poor in dispersibility and/or solubility in the dissolution test and shows low dissolution rate. On the other hand, preparations of Examples 1, 2 and 4 wherein a surfactant is added after pulverization according to the present invention showed improved dispersibility and/or solubility and high dissolution percentage.

Test Example 3

With respect to preparations of Example 3 and Comparative Example 3, each one tablet (amount of 100 mg calculated on the basis of cilostazol) was orally administered to beagle dogs (4 dogs per group) under fasting. Then, blood was collected with a lapse of time and cilostazol concentration in blood was measured. An average cilostazol concentration in blood is shown in Table 13 and average pharmacokinetic parameters after administration are shown in Table 14.

TABLE 13

Change in CLZ concentration in blood after oral administration to beagle dogs under fasting

| | CLZ concentration in blood (ng/mL) | | | | | | | | |
| --- | --- | --- | --- | --- | --- | --- | --- | --- | --- |
| | 0 | 0.25 | 0.5 | 1 | 2 | 3 | 4 | 6 | 8 | 10 |
| Example 3 | 0 | 87 | 89 | 204 | 1401 | 1297 | 923 | 373 | 147 | 32 |
| Comp. Example 3 | 0 | 0 | 5 | 174 | 264 | 198 | 179 | 94 | 48 | 15 |

TABLE 14

CLZ pharmacokinetic parameters after oral administration to beagle dogs under fasting

|  | AUC$_{0-10\,hr}$ (ng · hr/ML) | Cmax (ng/mL) | Tmax (hr) |
| --- | --- | --- | --- |
| Example 3 | 5360 (4.6) | 1465 (4.9) | 2.5 |
| Comp. Example 3 | 1160 (1.0) | 297 (1.0) | 2.25 |

Note 1: "AUC$_{0-10\,hr}$" means an amount of cilostazol absorbed within ten hours after administration, and a numeral in parenthesis denotes a magnification in case where a value of Comparative Example 3 is 1.0.
Note 2: "C$_{max}$" means the maximum cilostazol concentration in blood, and a numeral in parenthesis denotes a magnification in case where a value of Comparative Example 3 is 1.0.
Note 3: "T$_{max}$" means a time required to arrive at the maximum cilostazol concentration in blood.

As is apparent from the results of Test Example 3, the tablet of Example 3 showed an increase in the amount of cilostazol absorbed as compared with Comparative Example 3.

Test Example 4

40 ml of the diluted suspension obtained in Example 6, one capsule obtained in Example 7 or 40 ml of a non-pulverized cilostazol suspension obtained in Comparative Example 4 (each amount corresponding to 100 mg of cilostazol) were orally administered to beagle dogs (4 dogs per group) under fasting. Then, blood was collected from the foreleg vein with a lapse of time for ten hours after administration and cilostazol concentration in plasma was determined. Pharmacokinetic parameters after administration are determined. The results are shown in FIG. 1 and Table 15.

TABLE 15 pharmacokinetic parameters after oral administration to beagle dogs under fasting

| Preparation samples | Pharmacokinetics parameter | | |
|---|---|---|---|
| | AUC (ng·hr/mL) | Cmax (ng/mL) | Tmax (hr) |
| Example 6 (wet-pulverized CLZ suspension) | 15733 | 4485 | 1.00 |
| Example 7 (spray-dried CLZ capsule) | 4763 | 1967 | 1.75 |
| Comp. Example 4 (CLZ suspension) | 655 | 223 | 1.75 |

Note 1: AUC means an area under the curve of drug concentration in blood versus time.
Note 2: $C_{max}$ means the maximum concentration in blood.
Note 3: $T_{max}$ means the time required to arrive at the maximum concentration in blood.

As is apparent from the results of Test Example 4, the wet-pulverized cilostazol suspension of Example 6 showed a drastic increase in drug concentration in plasma as compared with the cilostazol suspension of Comparative Example 4, and the absorption rate increased by 20 or more time. In case where the capsule of the spray-dried powder of wet-pulverized cilostazol is administered (Example 7), the absorption rate was increased by about seven times as compared with the cilostazol suspension (Comparative Example 4).

Test Example 5

Cilostazol Dissolution Test of Examples 13 and 18

Test procedure: Using 900 mL of an aqueous 0.4% SLS solution as a test solution, a test was carried out at 75 rpm by a Paddle method. The results are shown in Table 16.

TABLE 16

| | Drug dissolution rate (%) | |
|---|---|---|
| Time (hr) | Example 13 | Example 18 |
| 0.0 | 0.0 | 0.0 |
| 1.0 | 6.6 | 8.8 |
| 2.0 | 16.4 | 20.6 |
| 3.0 | 26.4 | 33.1 |
| 4.0 | 35.8 | 45.1 |
| 5.0 | 45.2 | 56.3 |
| 6.0 | 54.3 | 66.7 |
| 8.0 | 71.1 | 84.9 |
| 10.0 | 86.5 | 97.8 |
| 12.0 | 96.7 | 102.2 |
| 14.0 | 100.5 | 103.7 |
| 16.0 | 101.3 | 103.7 |

Test Example 6

Cilostazol Dissolution Test

With respect to the dry powder obtained in Example 35 (containing cilostazol in the amount of 100 mg), the test was carried out at 75 rpm by a Paddle Method using an aqueous 0.3% SLS solution as a test solution. The dissolution rate measured after two minutes from the beginning of the test is shown in Table 17.

TABLE 17

Results of cilostazol dissolution test

| Dry powder | Dissolution rate (%) after two minutes |
|---|---|
| P-1 | 83.4 |
| P-2 | 82.0 |
| P-3 | 80.4 |
| P-4 | 62.2 |
| P-5 | 75.1 |

Test Example 7

Cilostazol Dissolution Test of Dry Coated Tablets P to U of Example 38

Figure 2:
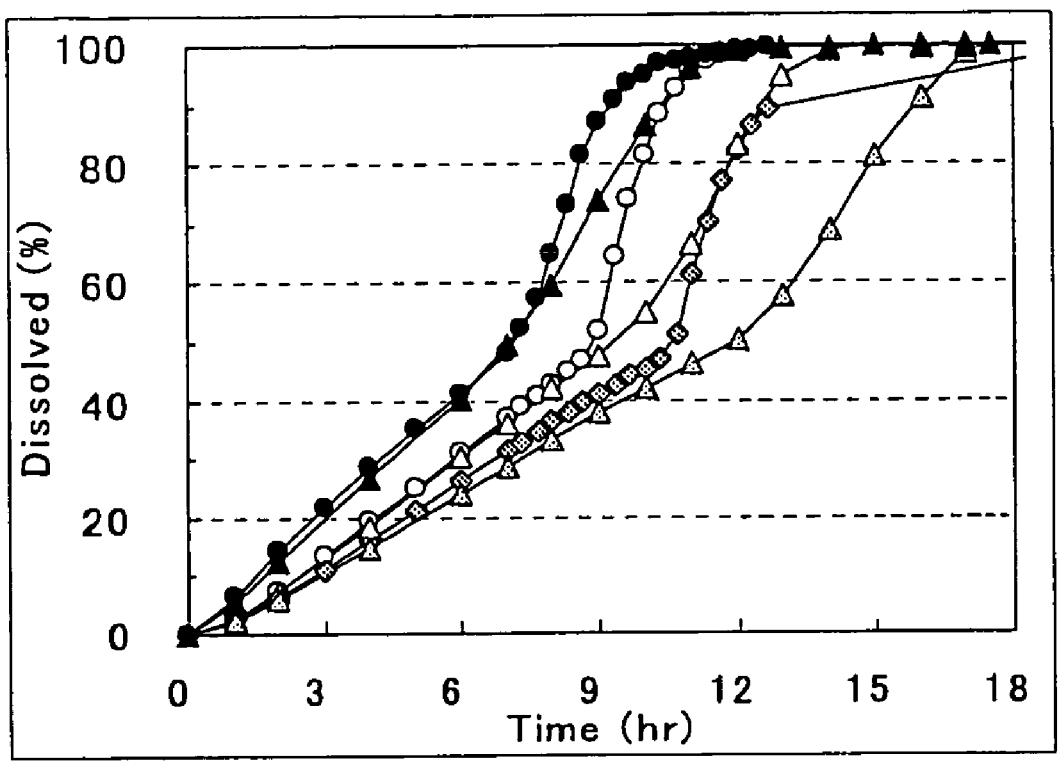
FIG. 2 is a graph showing a relation between the dissolved rate (%) of cilostazol and time (hr) when the dissolution test was carried out in Test Example 7 using dry coated tablets P to U containing cilostazol obtained by Example 38.
Figure 3:
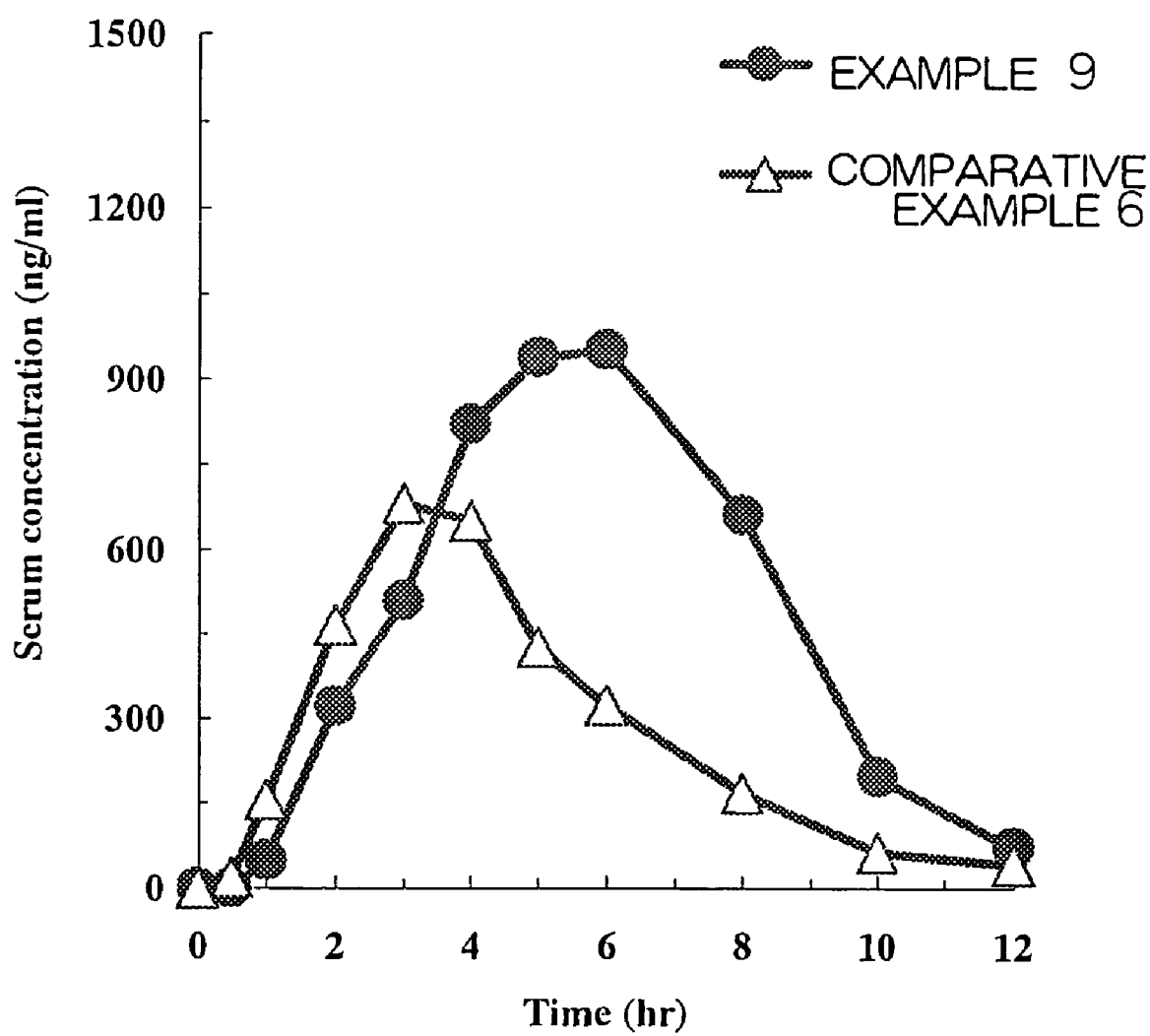
FIG. 3 is a graph showing a change in concentration of a drug in plasma after preparations of Example 9 and Reference Example 6 were orally administered to beagle dogs in Test Example 9.

Test procedure: Using 900 mL of an aqueous 0.4% SLS solution as a test solution, a test was carried out at 75 rpm by a Puddle process. The results are shown in FIG. 2.

Test Example 8

Absorption Test of Slightly Soluble Drug at Upper and Lower Portions of the Digestive Tract.

In the same manner as in Test Example 1, preparations of Example 2 and Comparative Examples 1 and 5 were directly administered in the duodenum and the large intestine of rats. Then, blood was collected with a lapse of time and cilostazol concentration in blood was measured. Pharmacokinetic parameters after administration are shown in Table 18.

TABLE 18

Cilostazol pharmacokinetic parameters

| Samples | Portion to be administered | Pharmacokinetics parameter | |
|---|---|---|---|
| | | AUC0-2 hr (ng·hr/mL) | Cmax (ng/mL) |
| Comp. Example 1 | Duodenum | 2591 | 1905 |
| Comp. Example 5 | Duodenum | 3682 | 3002 |
| Comp. Example 1 | Large intestine | 186 | 170 |
| Comp. Example 5 | Large intestine | 236 | 168 |
| Example 2 | Duodenum | 3959 | 2960 |
| Example 2 | Large intestine | 1910 | 1588 |

It has been known that the solubility of slightly soluble drugs is improved and bioavailability is increased when the drug is pulverized thereby to reduce the particle diameter. However, as a result of regional absorption study, it has been found that some slightly soluble drugs (e.g. cilostazol) showed increased bioavailability by pulverization only in the upper portion of the digestive tract. The bioavailability of these drugs in the lower portion of the digestive tract could be improved only by the combination of pulverization of the drugs and addition of dispersing and/or solubilizing agent. The bioavailability in the upper portion of the digestive tract was not affected even if the combination method was applied. It has been recognized that a water-soluble polymer or surfactant is effective for use as the dispersing and/or solubilizing agent to be added.

Test Example 9

In the same manner as in Test Example 3, dry coated tablets of Example 9 and Comparative Example 6 were orally administered to beagle dogs. As the results, changes of concentration of cilostazol in plasma were shown in FIG.

3. Then, blood was collected with a lapse of time and cilostazol concentration in blood was measured. Pharmacokinetic parameters after administration are shown in Table 19.

TABLE 19

Cilostazol pharmacokinetics parameter

| Dry coated tablets | Pharmacokinetics parameter | |
|---|---|---|
| | AUCO-12 hr (ng · hr/mL) | Cmax (ng/mL) |
| Comp. Example 6 | 3348 | 924 |
| Example 9 | 5846 | 1180 |

As is apparent from the results of Test Example 9, the dry coated tablet of Example 9 showed an increase in the amount of cilostazol absorbed as compared with that of Comparative Example 6. The tablet of Comparative Example 6 showed a lower absorbability with the lapse of time and a lower concentration of cilostazol in blood, while the tablet of Example 9 showed a sustaining absorbability of cilostazol and its concentration in blood was continued in a high level.

Test Example 10

Figure 4:
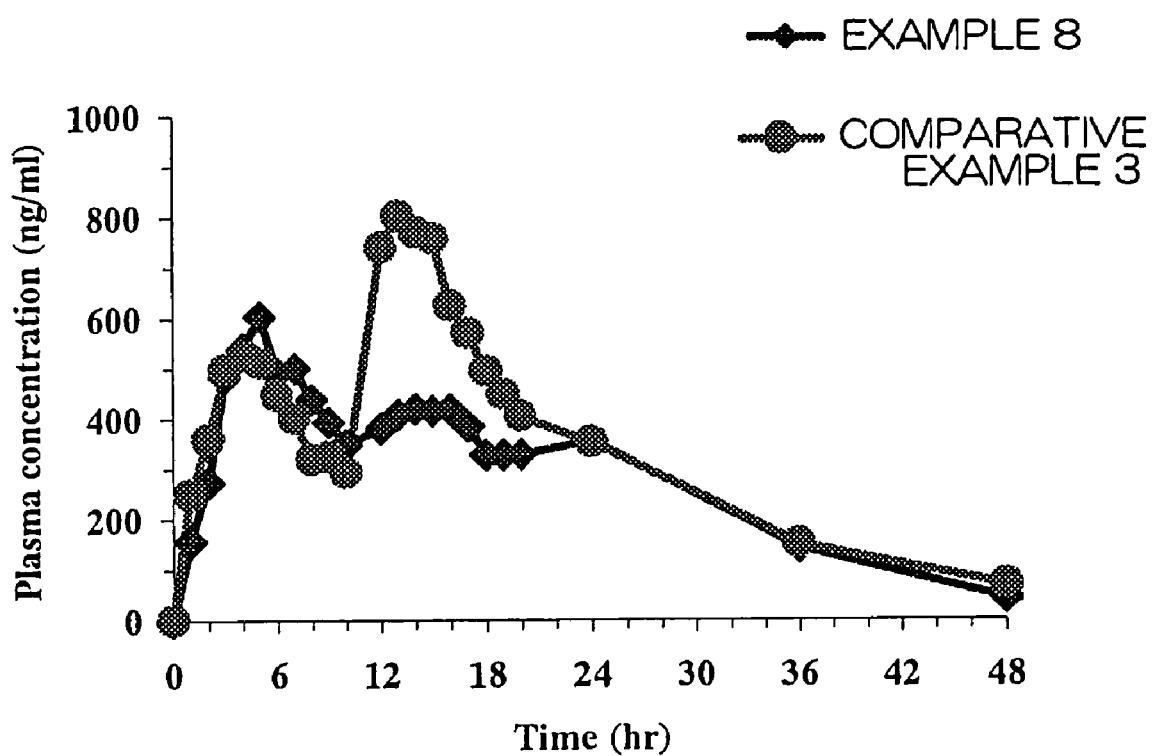
FIG. 4 is a graph showing a relation between cilostazol concentration in plasma and time when sustained release preparations of cilostazol obtained in Example 8 were orally administered to healthy male adults in Test Example 10.
Figure 5:
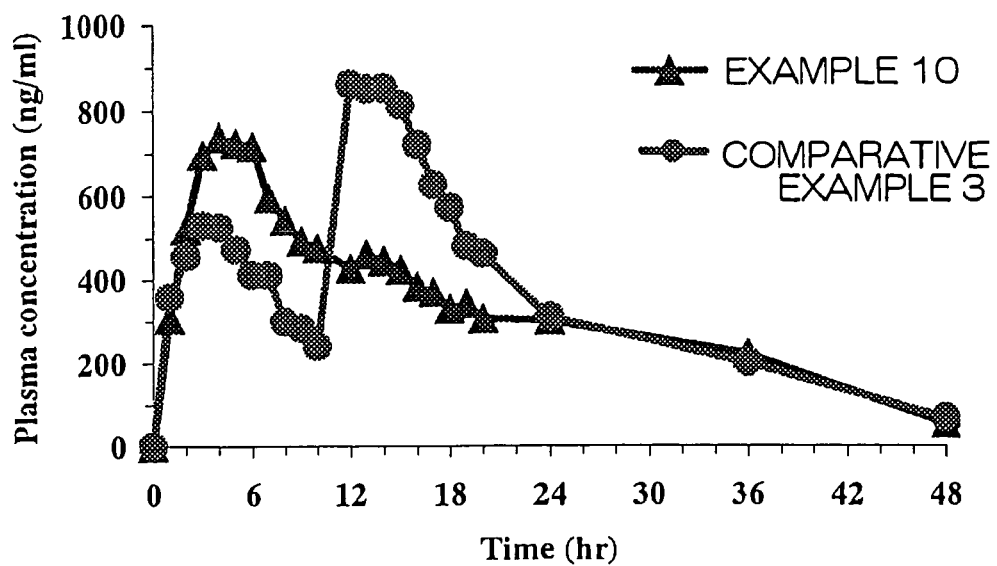
FIG. 5 is a graph showing a relation between cilostazol concentration in plasma and time when sustained release preparations of cilostazol obtained in Example 10 were orally administered to healthy male adults in Test Example 10.
Figure 6:
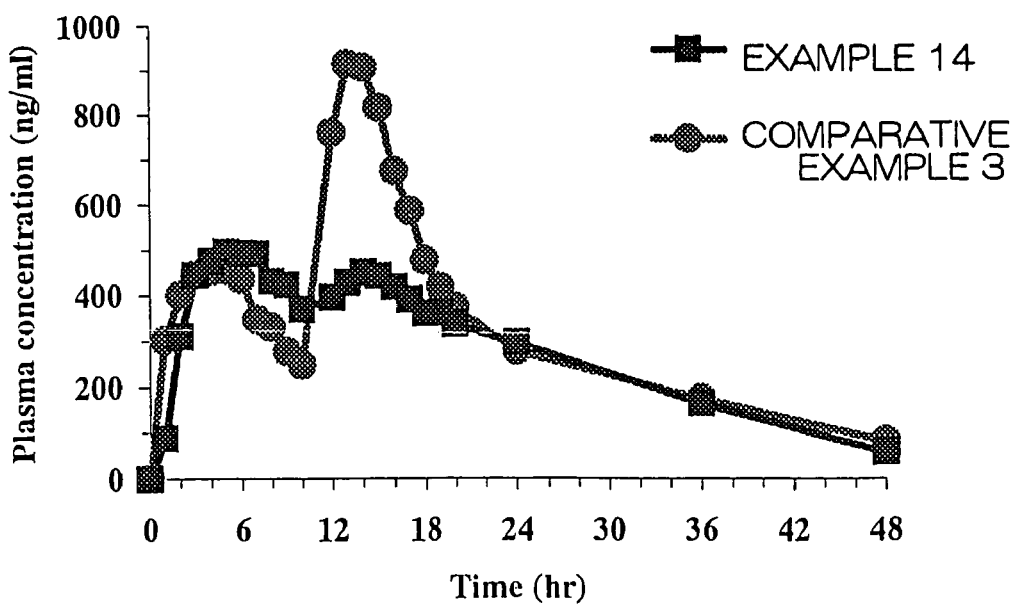
FIG. 6 is a graph showing a relation between cilostazol concentration in plasma and time when sustained release preparations of cilostazol obtained in Example 14 were orally administered to healthy male adults in Test Example 10.

Using three-arm two-period cross over design, the immediate release preparation in Comparative Example 3 and three cilostazol sustained release preparations in Example 8, 10 and 14 were administered orally to nine healthy male adults under fasting conditions. The preparation of Comparative Example 3 (corresponding to 100 mg of cilostazol) was administered twice a day and sustained release preparations (corresponding to 200 mg of cilostazol) were administered once a day. Five or more days after the first administration, the second administration was given. After the completion of the administration, blood was collected with a lapse of time and cilostazol concentration in plasma was measured. Graphs showing change in concentration in plasma are shown in FIGS. 4, 5 and 6, and pharmacokinetic parameters are shown in Tables 20, 21 and 22.

TABLE 20

| Sample | Cmax (ng/ml) | AUCO-t (ng · hr/ml) |
|---|---|---|
| Comp. Example 3 | 904 | 16227 |
| Example 8 | 699 | 14023 |

TABLE 21

| Sample | Cmax (ng/ml) | AUCO-t (ng · hr/ml) |
|---|---|---|
| Comp. Example 3 | 897 | 17406 |
| Example 10 | 828 | 15869 |

TABLE 22

| Sample | Cmax (ng/ml) | AUCO-t (ng · hr/ml) |
|---|---|---|
| Comp. Example 3 | 975 | 15790 |
| Example 14 | 597 | 11450 |

INDUSTRIAL APPLICABILITY

A cilostazol fine-powdered preparation obtained by subjecting cilostazol as an active ingredient and a dispersing and/or solubilizing agent to dry or wet pulverization, or a cilostazol fine-powdered preparation obtained by using a bulk cilostazol pulverized powder and a dispersing and/or solubilizing agent in combination shows drastically improved absorption from the lower portion of the digestive tract, and has an effect of being absorbed for a long period of time and sustaining a desired blood concentration for a long period of time. Furthermore, the preparation has such a characteristic that unfavorable side effects such as headache, caused by high blood concentration due to absorption in a short period of time immediately after oral administration of a conventional cilostazol preparation, is inhibited by forming into a sustained release preparation.

The invention claimed is:

1. A cilostazol preparation for oral administration which is capable of dissolving at the lower portion of a human digestive tract, comprising a fine powder of cilostazol having an average particle diameter of from 2 to 10 μm as an active ingredient, wherein said fine powder has been incorporated into a surfactant as a dispersing and/or solubilizing agent and wherein the preparation is in the form of powder, a granule, a pill, a tablet or a capsule for orally administering the preparation to a human.

2. The cilostazol preparation according to claim 1, wherein said dispersing and/or solubilizing agent is incorporated within a range from 0.005 to 50 parts by weight based on 1 part by weight of cilostazol.

3. The cilostazol preparation according to claim 2, wherein said surfactant is one or more selected from the group consisting of polyglycerin fatty acid ester, polyoxyethylene sorbitan fatty acid ester, polyethylene glycol fatty acid ester, polyoxyethylene alkyl ether, polyoxyethylene castor oil, surcrose ester of fatty acid and alkyl sulfate salt.

4. The cilostazol preparation according to claim 3, wherein said surfactant is one or more selected from the group consisting of polyoxyethylene sorbitan fatty acid ester, polyoxyethylene alkyl ether and alkyl sulfate salt.

5. The cilostazol preparation according to claim 4, wherein said surfactant is an alkyl sulfate salt.

6. The cilostazol preparation according to claim 3, wherein said fine powder of cilostazol is a fine powder having an average particle diameter of from 2 to 7 μm.

7. The cilostazol preparation according to claim 6, wherein said dispersing and/or solubilizing agent is incorporated within a range from 0.01 to 10 parts by weight based on 1 part by weight of cilostazol.

8. The cilostazol preparation according to claim 6, wherein said fine powder of cilostazol is a fine powder having an average particle diameter of from 2 to 5 μm.

9. The cilostazol preparation according to claim 6, wherein said surfactant is one or more selected from the group consisting of polyoxyethylene sorbitan fatty acid ester, polyoxyethylene alkyl ether and alkyl sulfate salt.

10. The cilostazol preparation according to claim 9, wherein said fine powder of cilostazol is a fine powder having an average particle diameter of from 2 to 5 μm.

11. The cilostazol preparation according to claim 10, wherein said surfactant is an alkyl sulfate salt.

12. The cilostazol preparation according to claim 11, wherein said alkyl sulfate salt is sodium lauryl sulfate.

13. A sustained release preparation of cilostazol which comprises any one of the cilostazol preparations of claims 1–12 coated with a sustained release coating material.

14. The sustained release preparation according to claim 13, which is a dry coated tablet comprising a sustained release outer layer portion containing cilostazol, and a sustained release core tablet containing the cilostazol preparation, wherein a solubility of said core tablet is more rapid than that of said outer layer portion.

15. The sustained release preparation according to claim 13, which is a tablet containing core granules wherein sustained release core granules containing the cilostazol preparation are coated with an enteric material and further said sustained release core granules are compressed with an outer layer portion containing cilostazol.

16. The sustained release preparation according to claim 13, which is a capsule comprising granules coated with an enteric material, wherein said granules contain the cilostazol preparation.

17. The sustained release preparation according to claim 13, which is a multiple-unit preparation containing more than two sustained release tablets containing the cilostazol preparation.

18. A sustained release preparation of cilostazol, which comprises a cilostazol preparation for oral administration which is capable of dissolving at the lower portion of a human digestive tract, comprising a fine powder of cilostazol having an average particle diameter of from 2 to 10 µm as an active ingredient, wherein said fine powder has been incorporated into a surfactant as a dispersing and/or solubilizing agent and wherein the preparation is in the form of powder, a granule, a pill, a tablet or a capsule for orally administering the preparation to a human.

19. A process of administering a cilostazol preparation for oral administration which is capable of dissolving at the lower portion of a human digestive tract, comprising administering to a human a sustained release preparation comprising a fine powder of cilostazol having an average particle diameter of from 2 to 10 µm as an active ingredient, wherein said fine powder has been incorporated into a surfactant as a dispersing and/or solubilizing agent and wherein the preparation is in the form of powder, a granule, a pill, a tablet or a capsule for orally administering the preparation to the human.

* * * * *